(12) United States Patent
Yamane

(10) Patent No.: US 11,877,820 B2
(45) Date of Patent: Jan. 23, 2024

(54) MICROSCOPE DRAPE AND METHOD OF ATTACHING THE SAME

(71) Applicant: MEILLEUR CO., LTD., Funabashi (JP)

(72) Inventor: Tsurashi Yamane, Funabashi (JP)

(73) Assignee: MEILLEUR CO., LTD, Funabashi (JP)

(*) Notice: Subject to any disclaimer, the term of this patent is extended or adjusted under 35 U.S.C. 154(b) by 0 days.

(21) Appl. No.: 18/024,092

(22) PCT Filed: May 23, 2022

(86) PCT No.: PCT/JP2022/021088
§ 371 (c)(1),
(2) Date: Mar. 1, 2023

(65) Prior Publication Data
US 2023/0372045 A1 Nov. 23, 2023

(51) Int. Cl.
*A61B 46/10* (2016.01)
*A61B 90/20* (2016.01)
*G02B 21/00* (2006.01)

(52) U.S. Cl.
CPC .............. *A61B 46/10* (2016.02); *A61B 90/20* (2016.02); *G02B 21/0012* (2013.01)

(58) Field of Classification Search
CPC ......... A61B 46/10; A61B 90/20; A61B 90/50; A61B 902/25; A61B 3/13; A61B 3/132; A61B 3/177; A61B 1/045; A61B 1/00149; A61B 1/00142; G02B 21/00; G02B 27/00; G02B 21/0012; G02B 21/22; G02B 21/18;
(Continued)

(56) References Cited

U.S. PATENT DOCUMENTS

| 4,266,663 A | 5/1981 | Geraci |
| 2005/0063058 A1 | 3/2005 | Langley |

(Continued)

FOREIGN PATENT DOCUMENTS

| CN | 112166364 A | 1/2021 |
| JP | 2010-512851 A | 4/2010 |

(Continued)

OTHER PUBLICATIONS

Jul. 19, 2022 International Search Report issued in International Patent Application No. PCT/JP2022/021088.
(Continued)

*Primary Examiner* — Jie Lei
(74) *Attorney, Agent, or Firm* — Oliff PLC

(57) ABSTRACT

A microscope drape capable of further facilitating an attachment operation thereof to a surgical microscope while keeping a clean condition. The microscope drape includes: a lens cap that is attached to and detached from a housing of an objective lens of a surgical microscope; a protective lens that is attached to the lens cap with being tilted with respect to an optical axis of the objective lens to protect the objective lens; and a drape main body that covers the surgical microscope. The drape main body includes: a bag-shaped portion having a bag shape whose one end is formed to be an opening, to which the lens cap is attached; and a band-shaped portion that extends to form a band shape from a portion in a circumferential direction of the opening of the bag-shaped portion.

3 Claims, 13 Drawing Sheets

(58) Field of Classification Search
CPC ... G02B 21/24; G02B 21/082; G02B 27/0006
USPC ......... 359/510, 507, 508, 511–514; 600/249, 600/122, 133, 109, 131
See application file for complete search history.

(56) References Cited

U.S. PATENT DOCUMENTS

| | | |
|---|---|---|
| 2005/0286130 A1 | 12/2005 | Bala |
| 2008/0144178 A1 | 6/2008 | Dillon et al. |
| 2009/0020357 A1 | 1/2009 | Pack-Walden et al. |
| 2014/0240832 A1 | 8/2014 | Nakamura et al. |
| 2017/0168292 A1 | 6/2017 | Koenig et al. |
| 2018/0310912 A1 | 11/2018 | Nordgren et al. |
| 2019/0282317 A1 | 9/2019 | Fields et al. |
| 2021/0405353 A1 | 12/2021 | Yamane et al. |

FOREIGN PATENT DOCUMENTS

| | | | |
|---|---|---|---|
| JP | 2012-183449 A | 9/2012 | |
| JP | 2014-161504 A | 9/2014 | |
| JP | 2017-107210 A | 6/2017 | |
| JP | 6749532 B1 * | 9/2020 | ............. A61B 46/10 |
| WO | 2022/003806 A1 | 1/2022 | |

OTHER PUBLICATIONS

Jul. 19, 2022 Written Opinion issued in International Patent Application No. PCT/JP2022/021088.
Sep. 6, 2022 Decision to Grant a Patent issued in Japanese Patent Application No. 2022-530254.
Aug. 23, 2022 Notice of Reasons for Refusal issued in Japanese Patent Application No. 2022-530254.
Jul. 12, 2022 Notice of Reasons for Refusal issued in Japanese Patent Application No. 2022-530254.

* cited by examiner

MICROSCOPE DRAPE AND METHOD OF ATTACHING THE SAME

TECHNICAL FIELD

The present invention relates to a microscope drape for covering a surgical microscope.

BACKGROUND ART

In neurosurgery, otorhinolaryngology, orthopedics, and ophthalmology, there are cases that surgery is performed using a surgical microscope to enlarge the surgical field. Surgery must be performed in a clean operation, however, since it is difficult to sterilize the surgical microscope itself, the surgical microscope is commonly covered with a disposable microscope drape to secure a clean field in each surgery (see, for example, Patent Literatures 1 to 4).

A typical microscope drape includes a lens cap to be attached to and detached from an objective lens of a surgical microscope, and a bag-shaped drape main body that holds the lens cap and covers the surgical microscope. Attachment of such a microscope drape to a surgical microscope without making the surface of the drape main body touch unclean portions (for example, surgical microscope, surrounding equipment, floor, operator, etc.) requires a skilled technique.

In order to solve the problem above, Patent Literature 5 discloses a drape main body including a band-shaped first drape for covering the upper portion of a surgical microscope, a band-shaped second drape for covering the lower portion of the surgical microscope, and a fastening portion for fastening the first drape and the second drape to each other.

CITATION LIST

Patent Literature

Patent Literature 1: JP-A-2012-183449
Patent Literature 2: JP-A-2014-161504
Patent Literature 3: JP-A-2010-512851
Patent Literature 4: JP-A-2017-107210
Patent Literature 5: WO-2022-003806

SUMMARY OF INVENTION

Technical Problem

The drape main body disclosed in Patent Literature 5 makes an attachment operation easier than the microscope drapes according to Patent Literatures 1 to 4, however, it does not completely avoid a risk that the band-shape second drape located below the surgical microscope touches the floor and gets unclean.

The present invention has been made in view of the problems above in the prior art, and an object of the present invention is to provide a microscope drape capable of further facilitating an attachment operation thereof to a surgical microscope while keeping a clean condition.

Solution to Problem

In order to solve the problems above, the present invention provides a microscope drape, comprising: a lens cap that is attached to and detached from a housing of an objective lens of a surgical microscope; a protective lens that is attached to the lens cap with being tilted with respect to an optical axis of the objective lens to protect the objective lens; and a drape main body that covers the surgical microscope, wherein the drape main body includes: a bag-shaped portion having a bag shape whose one end is formed to be an opening, to which the lens cap is attached; and a band-shaped portion that extends to form a band shape, from a portion in a circumferential direction of the opening of the bag-shaped portion.

Advantageous Effects of Invention

According to the present invention, it is possible to obtain a microscope drape capable of further facilitating an attachment operation thereof to a surgical microscope while keeping a clean condition.

DESCRIPTION OF EMBODIMENTS

Hereinafter, a microscope drape 10 according to an embodiment will be described with reference to the drawings. It should be noted that the embodiment of the present invention described below is an example for embodying the present invention, and the scope of the present invention is not limited to the scope of the description of the embodiment. Therefore, the present invention can be implemented with various modifications to the embodiment.

Figure 1:
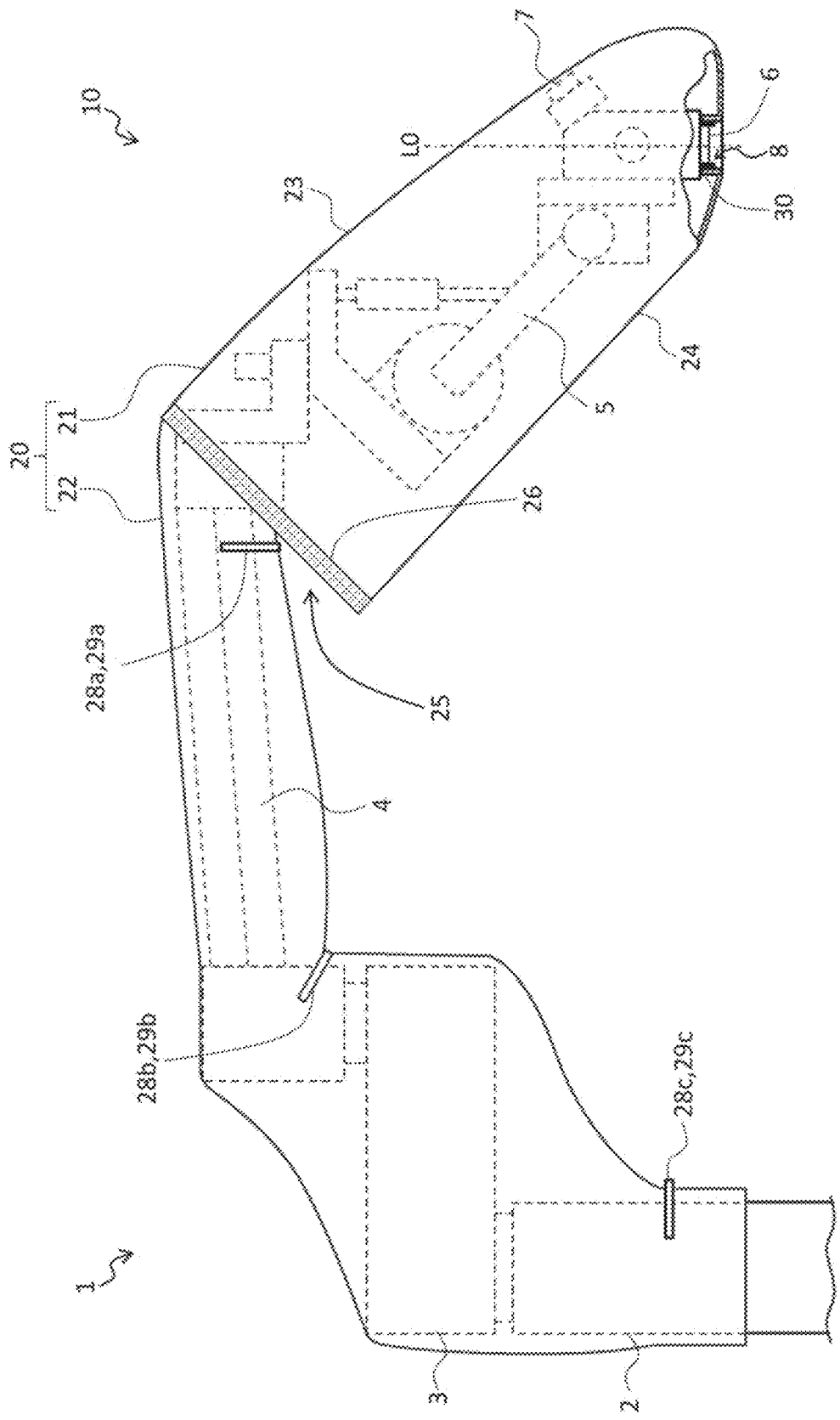
FIG. 1 is a schematic diagram of a main part of a surgical microscope and a microscope drape.

FIG. 1 is a schematic diagram of a main part of a surgical microscope 1 and the microscope drape 10. As illustrated in FIG. 1, the surgical microscope 1 mainly includes a plurality of arms 2, 3, 4, 5 rotatably connected to each other, an objective lens 6 attached to the distal end of the arm 5, and an eyepiece lens 7. Rotation of the joint portions of the arms 2 to 5 relative to each other causes the objective lens 6 to be placed at a position facing the surgical field. In this state, the physician (surgeon) looks through the eyepiece 7, whereby he or she can observe the enlarged surgical field.

The objective lens 6 is a convex lens. The objective lens 6 is attached to the inside of a cylindrical housing 8. That is, an optical axis L0 of the objective 6 illustrated by an alternate long and short dash line in FIG. 1 corresponds to the axial direction of the housing 8.

The surgical microscope 1 further includes an illumination device (for example, LED, xenon lamp). A light irradiated from the illumination device passes through the objective lens 6 via an optical system (lens, mirror, and the like) housed in the arms 2 to 5, and is irradiated toward the surgical field. This light is reflected by the surgical field and enters the objective lens 6 again, whereby the physician can observe the surgical field. An irradiation direction of the light by the illumination device is tilted by, for example, about 3° to 6° with respect to the optical axis L0.

All equipment that touches or possibly touches the surgical field during surgery must be sterilized. However, since it is difficult to sterilize the surgical microscope 1 itself, surgical microscope 1 is covered with the disposable microscope drape 10 in each operation. The microscope drape 10 is packaged in a sterilized state, and an operator unpacks the microscope drape 10 in an operating room and covers it on the surgical microscope 1.

Figure 2:
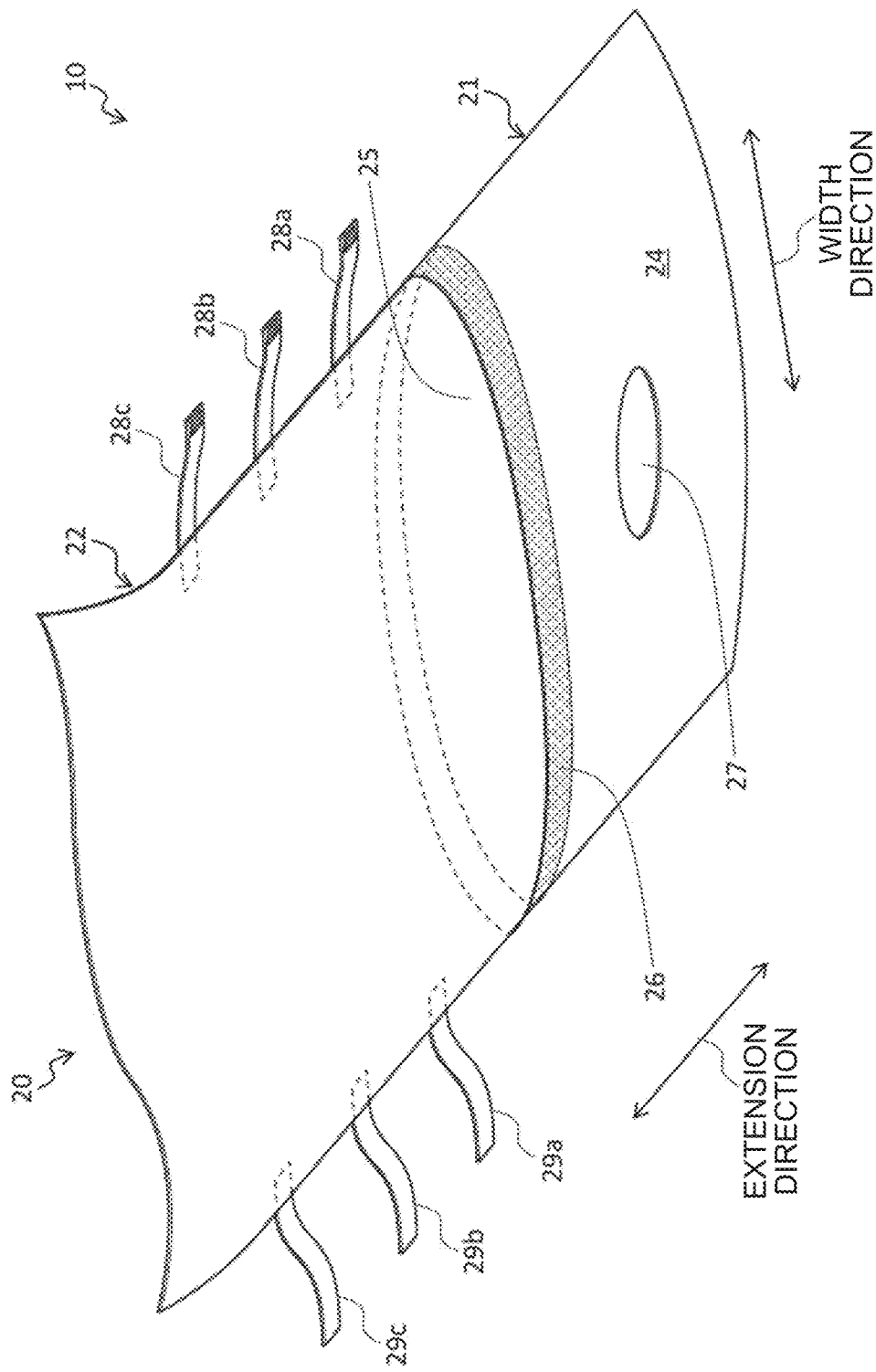
FIG. 2 is a bottom side perspective view of a microscope drape.
Figure 3:
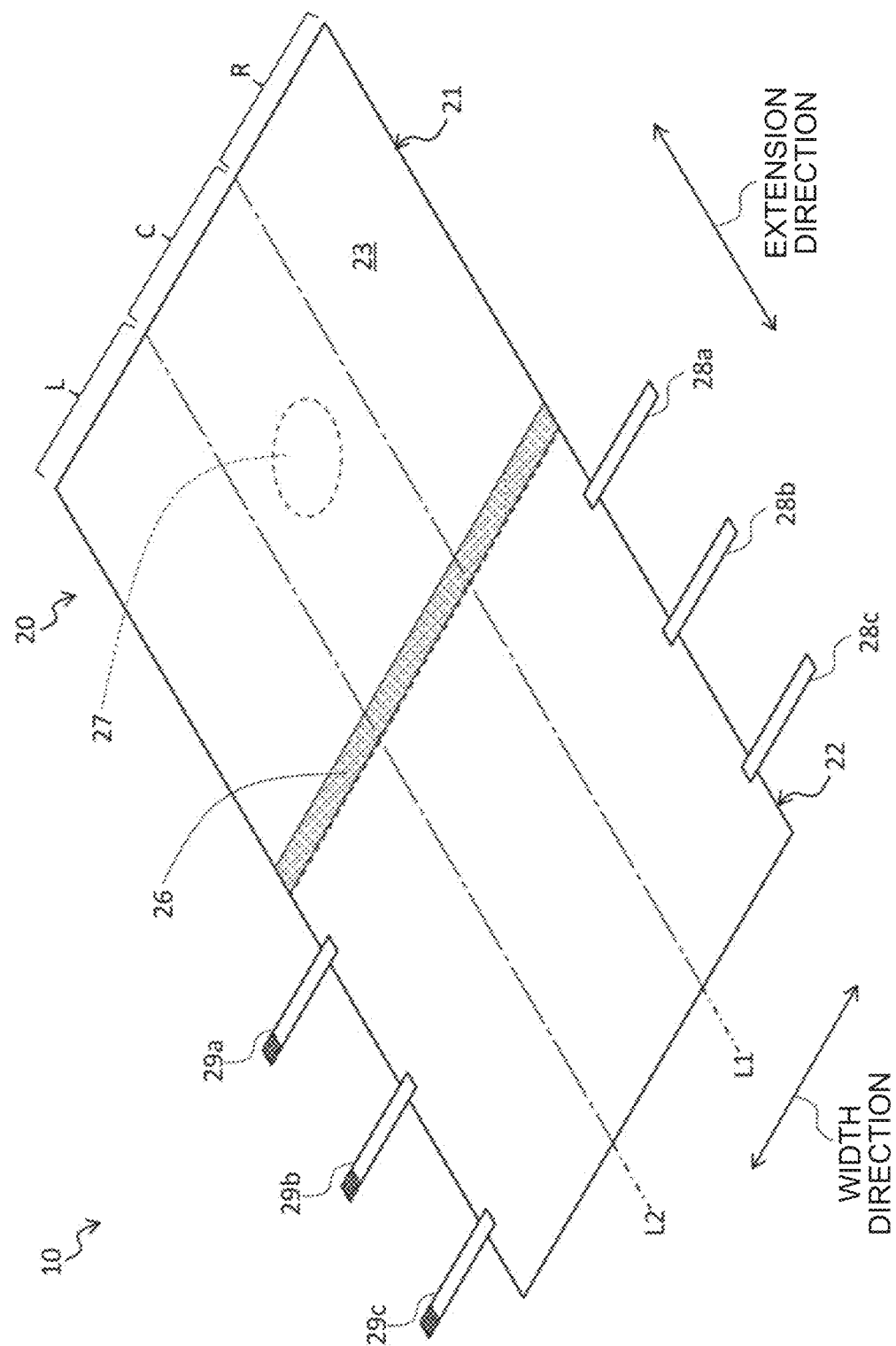
FIG. 3 is a top side perspective view of a microscope drape.

FIG. 2 is a bottom side perspective view of the microscope drape 10. FIG. 3 is a top side perspective view of the microscope drape 10. As illustrated in FIG. 1 to FIG. 3, the microscope drape 10 according to the present embodiment mainly includes a drape main body 20 and a lens cap unit 30. In FIG. 2 and FIG. 3, the lens cap unit 30 is not illustrated.

The drape main body 20 is a sheet-like member formed of a transparent or translucent material (for example, polyethylene). As illustrated in FIG. 1 to FIG. 3, the drape main body 20 includes a bag-shaped portion 21 and a band-shaped portion 22. The drape main body 20 has a rectangular external shape having a longitudinal direction (corresponding to "extension direction") and a short-length direction (corresponding to "width direction"). The extension direction and the width direction are directions perpendicular to each other in the plane perpendicular to the thickness direction of the drape main body 20.

The bag-shaped portion 21 is a portion having a shape like a bag, in which sheets are doubled and overlapped to each other. More specifically, the bag-shaped portion 21 includes an upper sheet 23 and a lower sheet 24 which overlap to each other. Each of the upper sheet 23 and the lower sheet 24 has a rectangular external shape. The three sides of the upper sheet 23 and the corresponding three sides of the lower sheet 24 are joined to each other, respectively. On the other hand, the other side of the upper sheet 23 and the other side of the lower sheet 24 are consecutive in the circumferential direction while being spaced apart from each other so as to define an opening 25.

The bag-shaped portion 21 is provided with a mark 26 indicating an outer edge of the opening 25. The mark 26 may be any mark such as a colored seal attached to the outer edge of the opening 25, a colored ink applied to the outer edge of the opening 25, or the like as long as it allows the operator to easily identify the outer edge of the opening 25 of the transparent or translucent drape main body 20.

The lower sheet 24 of the bag-shaped portion 21 is provided with a through hole 27. The through hole 27 passes through the lower sheet 24 in the thickness direction. The through hole 27 is formed substantially in the center of the lower sheet 24. The lens cap unit 30 is to be attached to the through hole 27, for example, by welding a portion defining the circumferential edge of the through hole 27 of the lower sheet 24 to the outer circumferential surface of the lens cap unit 30.

The band-shaped portion 22 extends along the longitudinal direction of the drape main body 20 from the side defining the opening 25 of the upper sheet 23. As illustrated in FIG. 1, in the case where the entire surgical microscope 1 has to be covered (for example, for surgical use), the band-shaped portion 22 is designed such that the length in the extension direction of the band-shaped portion 22 is more than that in the width direction thereof. Note that FIG. 2 and FIG. 3 illustrate the band-shaped portion 22 having the shortened length in the extension direction. On the other hand, in the case where simply the periphery of the objective lens 6 of the surgical microscope 1 needs to be draped (for example, for ophthalmic use), the length in the extension direction of the band-shaped portion 22 may be less than that in the width direction thereof.

In the band-shaped portion 22, both the sides in the width direction are provided a plurality of coupling members 28*a*, 28*b*, 28*c*, 29*a*, 29*b*, 29*c*. More specifically, in the band-shaped portion 22, the coupling members 28*a* to 28*b* are attached on one of the sides in the width direction with being spaced apart to each other in the extension direction by a predetermined distance, and the coupling members 29*a* to 29*b* are attached on the other side in the width direction with being spaced apart to each other in the extension direction by a predetermined distance.

As illustrated in FIG. 1, making the band-shaped portion 22 extend along the top surface of the surgical microscope 1 and coupling the corresponding coupling members 28*a* and 29*a*, 28*b* and 29*b*, and 28*c* and 29*c* to each other, respectively, enables the surgical microscope 1 to be covered with the band-shaped portion 22. The coupling members 28*a* to 28*c* and 29*a* to 29*c* may be any member, such as strings, snap buttons, zip fasteners, hook-and-loop fasteners, elastic strings, or the like as long as they can be coupled to one another.

In the description above, the drape main body 20 is divided into the bag-shaped portion 21 formed by the upper sheet 23 and the lower sheet 24 and the band-shaped portion 22. However, the drape main body 20 does not have to be formed by joining the independent upper sheet 23, lower sheet 24, and band-shaped portion 22 to each other. For example, the drape main body 20 may be formed by folding back a portion in the extension direction of the band-shaped sheet and welding both ends in the width direction of the overlapping portion. In this case, among the three joined sides of the upper sheet 23 and lower sheet 24, one of the sides corresponds to the portion of the band-shaped sheet which has been folded back, and the two of the sides correspond to the portions which have been welded.

That is, the bag-shaped portion 21 is sufficient as long as it is formed in the shape of a bag provided with the opening 25 at one end thereof. The band-shaped portion 22 is sufficient as long as it is formed to extend from a portion in the circumferential direction of the opening 25 of the bag-shaped portion 21. In the bag-shaped portion 21, an area in which the band-shaped portion 22 is formed is the upper sheet 23, and the other area is the lower sheet 24.

Figure 4:
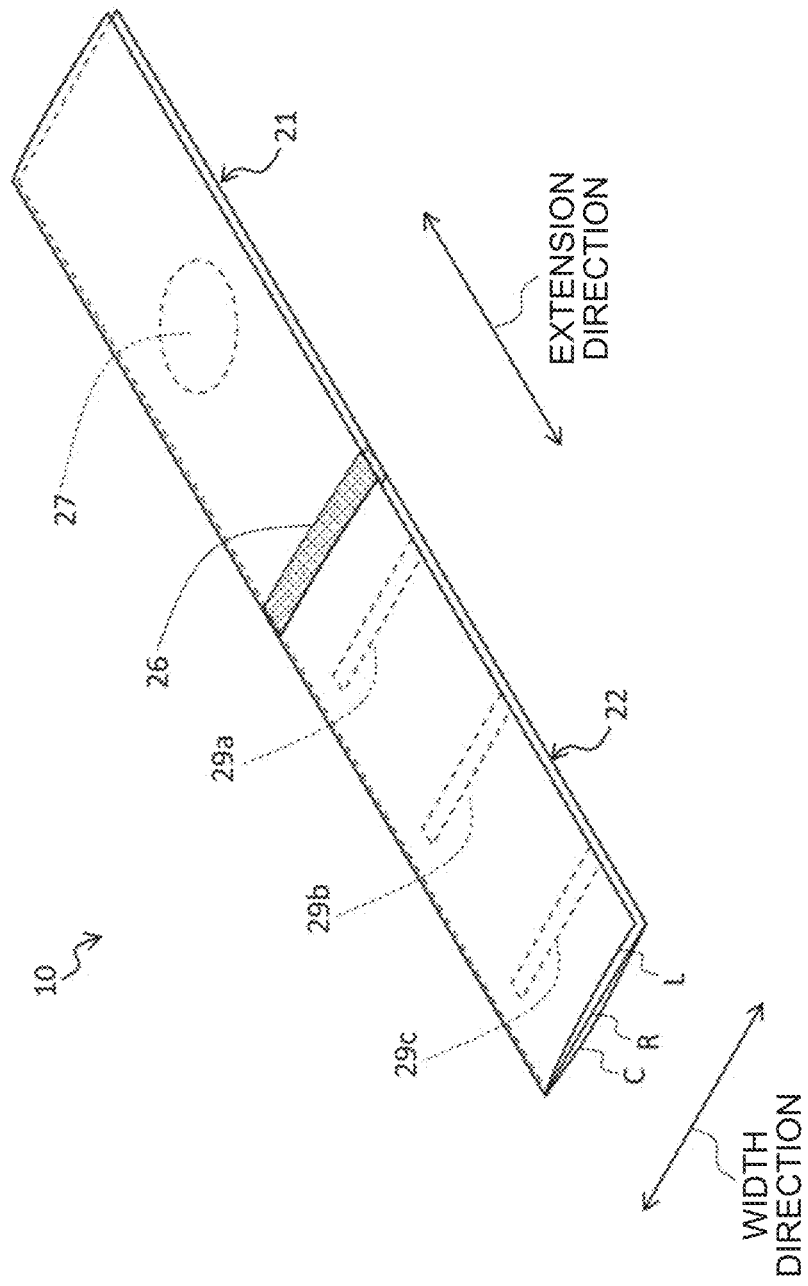
FIG. 4 illustrates a microscope drape folded in three.

FIG. 4 illustrates the microscope drape 10 folded in three. The microscope drape 10 is folded back along imaginary lines L1, L2 extending in the extension direction from positions spaced apart to each other in the widthwise direction, respectively, as illustrated in FIG. 3, thereby being folded in three as illustrated in FIG. 4. Hereinafter, in the drape main body 20, the area in the central portion between the imaginary lines L1, L2 is referred to as "area C", and the areas in both end portions adjacent the area C with the imaginary lines L1, L2 interposed therebetween are referred to as "area R" and "area L".

In the areas C, R, L, the size in the width direction of substantially corresponds to each other. The attachment position of the lens cap unit 30 (that is, position of the through-hole 27) is included in the area C. The area R is folded back toward the upper sheet 23 along the imaginary line L1, and thereafter, the area L is folded back toward the upper sheet 23 along the imaginary line L2. As a result, the microscope drape 10 is folded in three so that the areas C, R, L overlap to each other as illustrated in FIG. 4. Note that the order of folding back the areas R, L may be the reversed.

Figure 5:
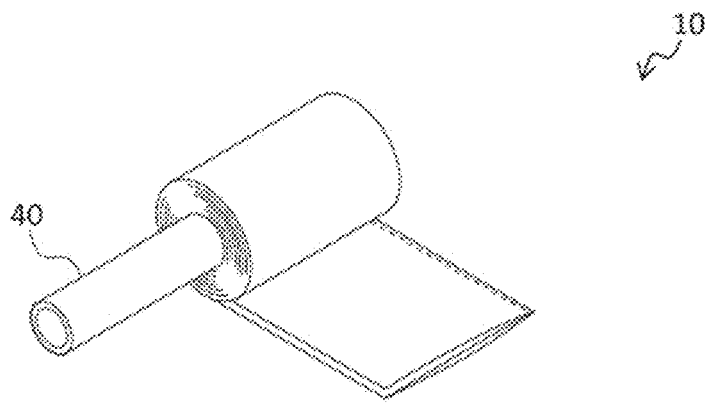
FIG. 5 illustrates that a microscope drape folded in three has been wound around a winding member.

FIG. 5 illustrates that the microscope drape 10 folded in three has been wound around a winding member 40. The winding member 40 is, for example, a rod-shaped member having a columnar shape (or cylindrical shape). The microscope drape 10 in the state as illustrated in FIG. 4 is wound around the winding member 40 from the extension end of the band-shaped portion 22 (end opposite to the bag-shaped portion 21) toward the bag-shaped portion 21 to be made to have a roll shape as illustrated in FIG. 5.

Preferably, the microscope drape 10 is wound around the winding member 40 such that the lens cap unit 30 is positioned on the outer circumferential surface of the roll. In other words, it is preferable that the winding member 40 is brought into contact with, in the microscope drape 10 folded in three, the side surface opposite to the side provided with the lens cap unit 30, and then made to wind it. Note that the winding direction may be reversed. The microscope drape 10 may be packaged in the wound state as illustrated in FIG. 5, or may be wound around the winding member 40 by the operator before being attached to the surgical microscope 1.

Figure 6:
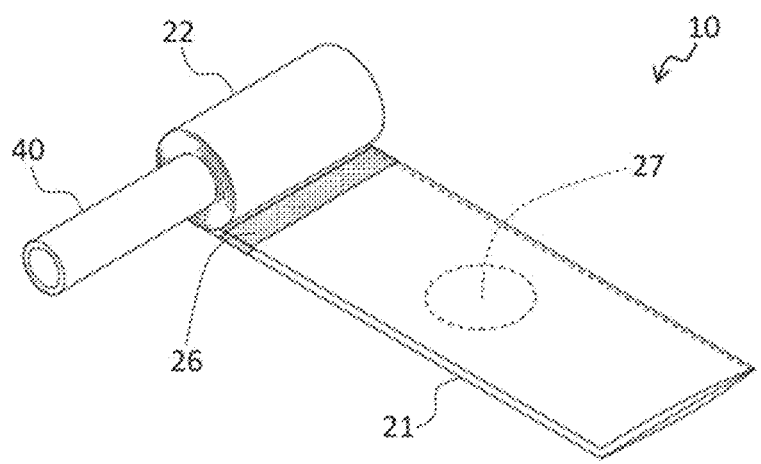
FIG. 6 illustrates a microscope drape immediately before being attached to a surgical microscope.
Figure 7:
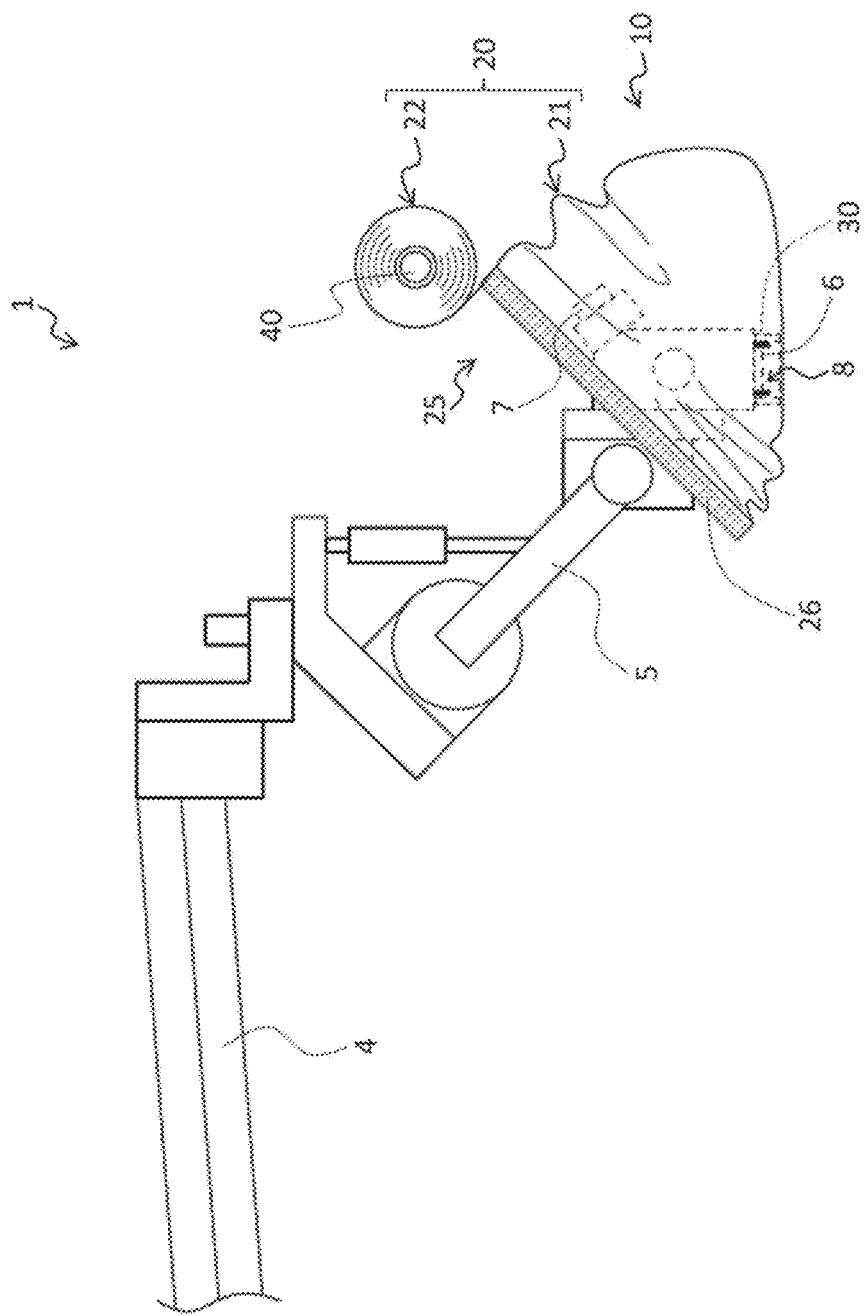
FIG. 7 illustrates that a lens cap unit attached to a housing.
Figure 8:
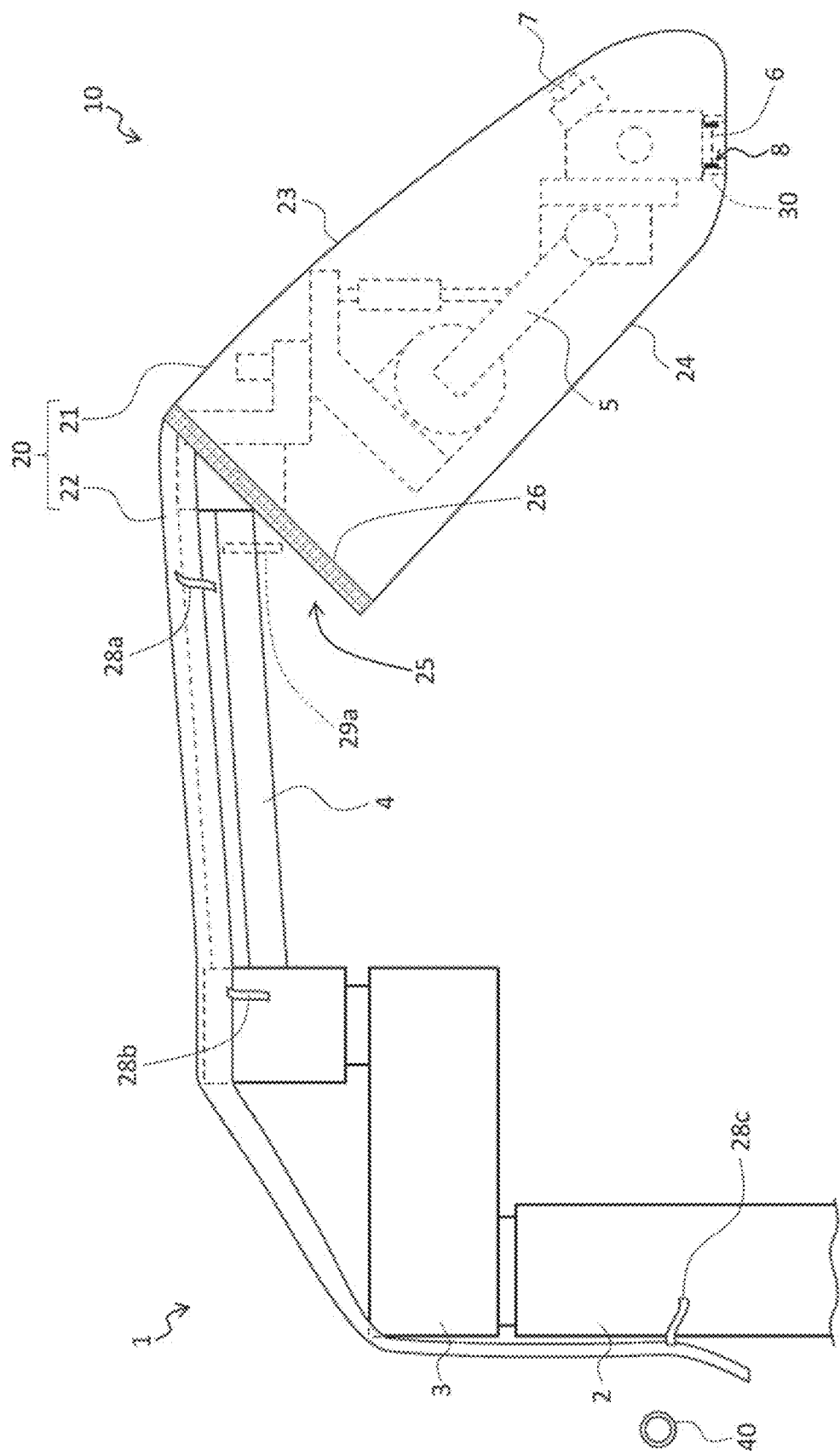
FIG. 8 illustrates a drape main body unwound from a winding member.
Figure 9:
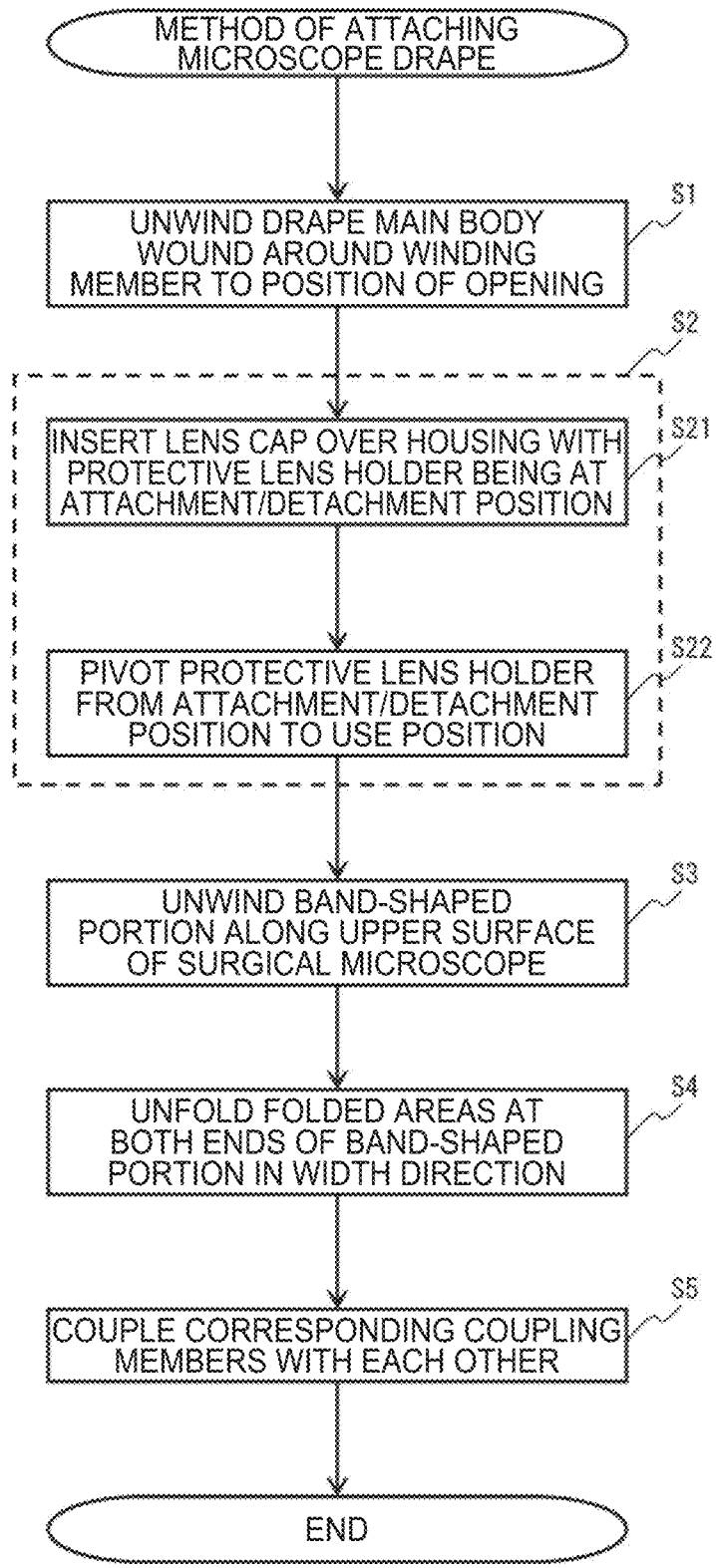
FIG. 9 illustrates a flowchart of a procedure for attaching a microscope drape to a surgical microscope.

Next, a method of attaching the microscope drape 10 to the surgical microscope 1 will be described with reference to FIG. 6 to FIG. 9. FIG. 6 illustrates the microscope drape 10 immediately before being attached to the surgical microscope 1. FIG. 7 illustrates the lens cap unit 30 attached to the housing 8. FIG. 8 illustrates the drape main body 20 unwound from the winding member 40. FIG. 9 illustrates a flowchart of a procedure (namely, attachment method) for attaching the microscope drape 10 to the surgical microscope 1.

Firstly, as illustrated in FIG. 6, the operator unwinds the drape main body 20 wound around the winding member 40 to the position of the opening 25 (S1). In other words, the operator unwinds, out of the bag-shaped portion 21 and the band-shaped portion 22, only the bag-shaped portion 21 from the winding member 40. For example, the operator may unwind the drape main body 20 from the winding member 40 until the mark 26 is exposed. This allows the folded areas R, L of the bag-shaped portion 21 to be unfolded in the width direction.

Next, as illustrated in FIG. 7, the operator makes the lens cap unit 30 be exposed from the inner side of the unfolded bag-shaped portion 21, and attaches it to the housing 8 of the objective lens 6 (S2). The shape of the lens cap unit 30 and the method of attaching it to the housing 8 will be described later with reference to FIG. 10 to FIG. 16.

Next, as illustrated in FIG. 8, the operator unwinds the band-shaped portion 22 from the winding member 40 along the upper surface of the surgical microscope 1 (S3). Then, the operator unfolds the folded areas R, L of the band-shaped portion 22 in the widthwise direction (S4). Thereafter, as illustrated in FIG. 1, in the state where the surgical microscope 1 is covered with the band-shaped portion 22, the operator couples the corresponding coupling members 28a and 29a, 28b and 29b, and 28c and 29c with each other, respectively (S5). Thus, the operation of attaching the microscope drape 10 to the surgical microscope 1 is completed.

Figure 10:
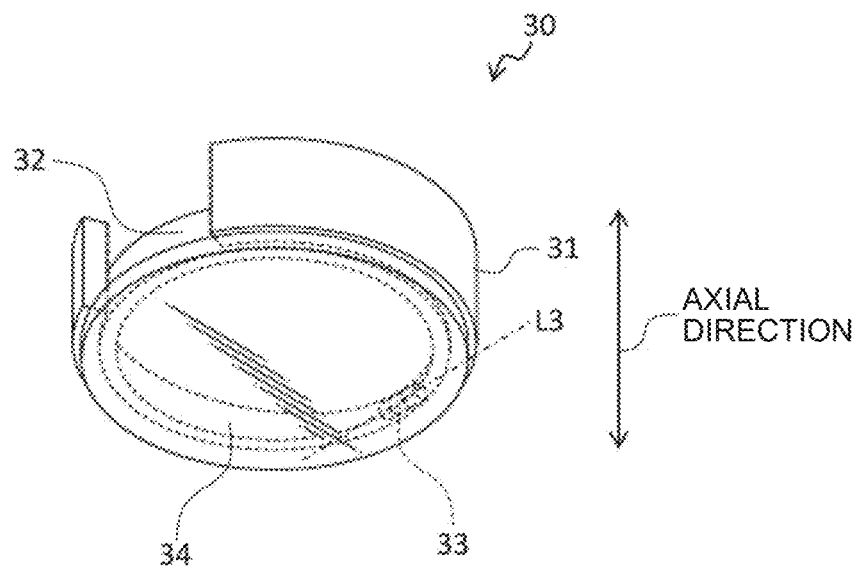
FIG. 10 is a bottom side perspective view of a lens cap unit with a protective lens holder being at an attachment/detachment position.
Figure 11:
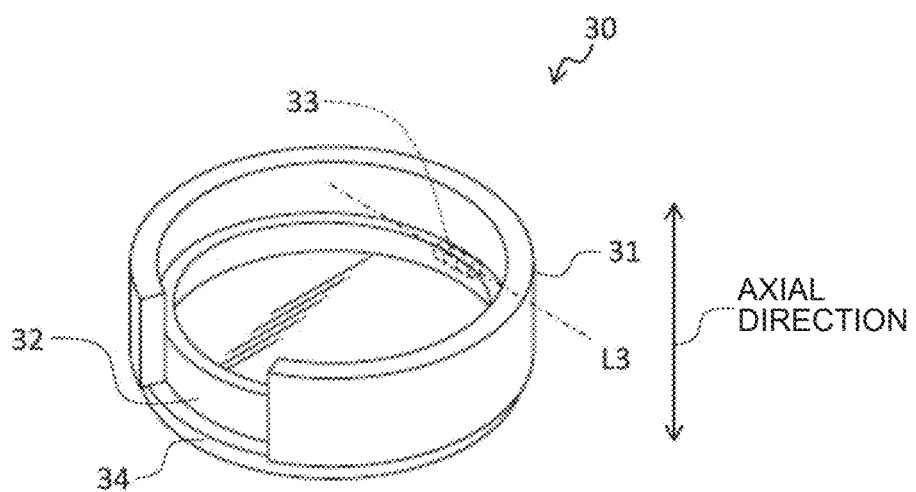
FIG. 11 is a top side perspective view of a lens cap unit with a protective lens holder being at an attachment/detachment position.
Figure 12:
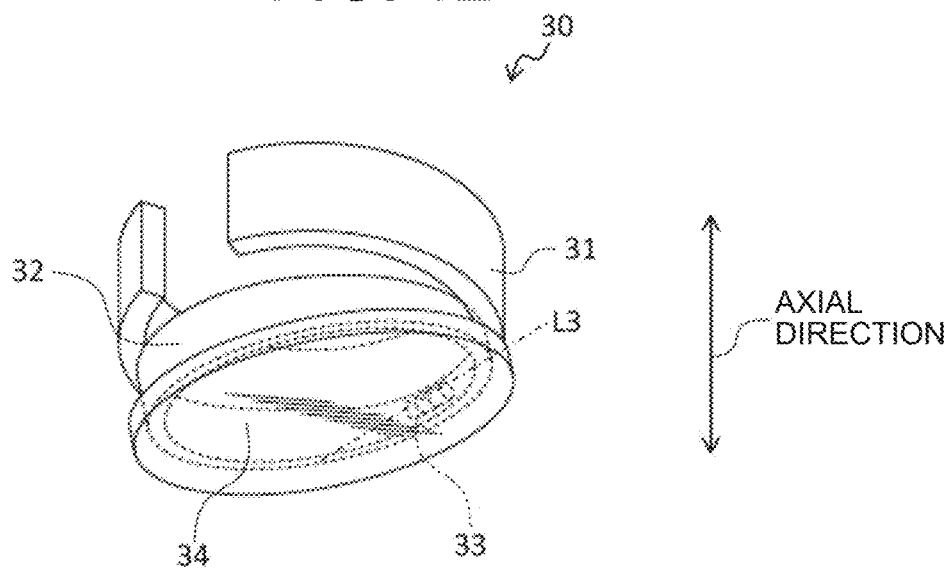
FIG. 12 is a bottom side perspective view of a lens cap unit with a protective lens holder being at a use position.
Figure 13:
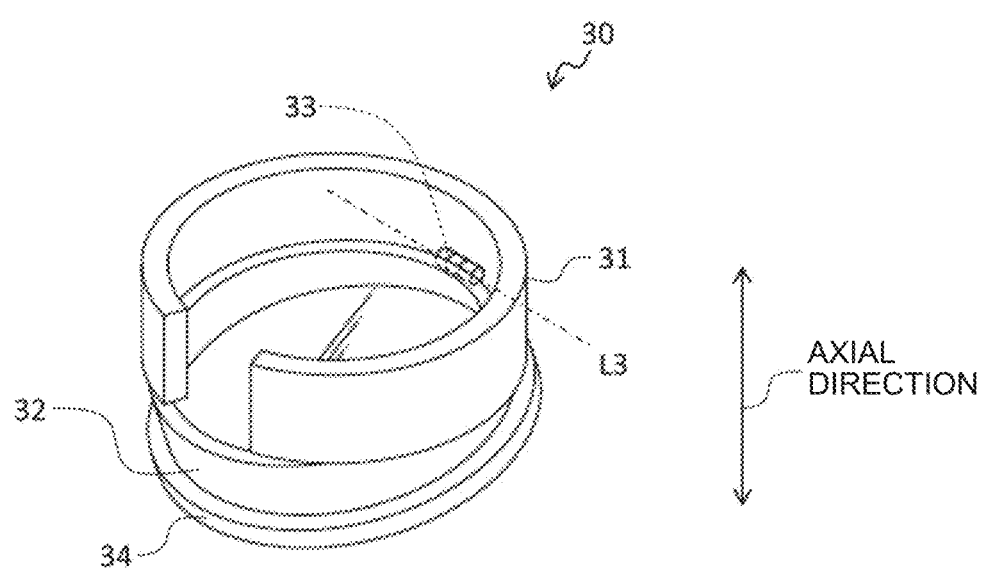
FIG. 13 is a top side perspective view of a lens cap unit with a protective lens holder being at a use position.

FIG. 10 is a bottom side perspective view of the lens cap unit 30 with a protective lens holder 32 being at the attachment/detachment position. FIG. 11 is a top side perspective view of the lens cap unit 30 with the protective lens holder 32 being at the attachment/detachment position. FIG. 12 is a bottom side perspective view of the lens cap unit 30 with the protective lens holder 32 being at the use position. FIG. 13 is a top side perspective view of the lens cap unit 30 with the protective lens holder 32 being at the use position.

As illustrated in FIG. 10 to FIG. 13, the lens cap unit 30 mainly includes a lens cap 31, the protective lens holder 32, a joint 33, and a protective lens 34. The lens cap unit 30 is attached to the through hole 27 of the drape main body 20. For example, the circumferential edge portion of the through hole 27 is welded with the outer circumferential surface of the protective lens holder 32 or protective lens 34. Alternatively, the protective lens holder 32 divided in the axial direction may sandwich the circumferential edge portion of the through-hole 27 between both sides in the thickness direction of the drape main body 20. That is, the lens cap 31 is indirectly attached to the drape main body 20 via the protective lens holder 32 or the protective lens 34.

The lens cap 31 is a member to be attached to and detached from the housing 8 of the objective lens 6. The lens cap 31 has the shape of a cylinder whose portion in the circumferential direction is opened. That is, the lens cap 31 has the arc-shaped (C-shaped) cross section perpendicular to the optical axis L0 (axial direction) of the objective lens 6. The lens cap 31 is formed of resin having elastic deformability (for example, polycarbonate, polyacetal, or the like). This enables the lens cap 31 to be elastically expand or contract so that the open portion touches or separates from each other.

The protective lens holder 32 has a cylindrical external shape. The size of the outside diameter of the protective lens holder 32 is set to be more than the size of the inside diameter of the lens cap 31 in the natural state (diameter is not expanded). One end (lower end in FIG. 14) of the protective lens holder 32 in the axial direction is perpendicular to the axial direction. On the other hand, the other end (upper end in FIG. 14) of the protective lens holder 32 in the axial direction is tilted with respect to the axial direction. That is, in the circumferential direction of the protective lens holder 32, the length of the protective lens holder 32 in the axial direction differs. The protective lens holder 32 holds the protective lens 34 at the one end in the axial direction. The protective lens holder 32 is pivotably attached to the lens cap 31 via the joint 33.

The joint 33 pivotably supports the protective lens holder 32 with respect to the lens cap 31 around a pivot axis L3 perpendicular to the optical axis L0. More specifically, the joint 33 is attached to the inner circumferential surface of the lens cap 31 and the position of the outer circumferential surface of the protective lens holder 32 whose length in the axial direction is the shortest. That is, in the circumferential direction of the cylinder of the protective lens holder 32, the length in the axial direction increases as the distance from the position of the joint 33 increases. The protective lens holder 32 pivots with respect to the lens cap 31 between the attachment/detachment position illustrated in FIG. 10 and FIG. 11 and the use position illustrated in FIG. 12 and FIG. 13.

The attachment/detachment position is a position of the protective lens holder 32 when the lens cap unit 30 is attached to or detached from the housing 8. At the attachment/detachment position, the protective lens holder 32 has entered the inside of the lens cap 31 to elastically expand the diameter of the lens cap 31. This makes the inside diameter of the lens cap 31 more than the expected size of the outside diameter of the housing 8. At the attachment/detachment position, the protective lens holder 32 holds the protective lens 34 with the protective lens 34 being perpendicular to the optical axis L0.

The use position is a position of the protective lens holder 32 when the surgical microscope 1 covered with the microscope drape 10 is used. At the use position, the protective lens holder 32 has been pulled out from the inside of the lens cap 31 to the opposite side of the objective lens 6, thereby reducing the diameter of the lens cap 31. This causes the inner circumferential surface of the lens cap 31 to be in close contact with the outer circumferential surface of the housing 8 so that the lens cap unit 30 is fixed to the housing 8. At the use position, the protective lens holder 32 tilts the protective lens 34 with respect to the optical axis L0.

The protective lens 34 is a flat-plate-shaped lens made of a material that transmits a light (for example, glass, resin, etc.). However, the protective lens 34 is not limited to the one having a flat plate shape, and may be a curved lens having a convex shape. The protective lens 34 is fixed to one end of the protective lens holder 32 in the axial direction. That is, the protective lens 34 is indirectly attached to the lens cap 31 via the protective lens holder 32 and the joint 33.

The protective lens 34 protects the objective lens 6 of the surgical microscope 1. More specifically, when the lens cap unit 30 is attached to the housing 8, the protective lens 34 faces the objective lens 6. Then, an external light that has passed through the protective lens 34 enters the objective lens 6. The protective lens 34 is tilted with respect to the optical axis L0 to prevent reflection and glare of the incident light of the surgical microscope 1.

Figure 14:
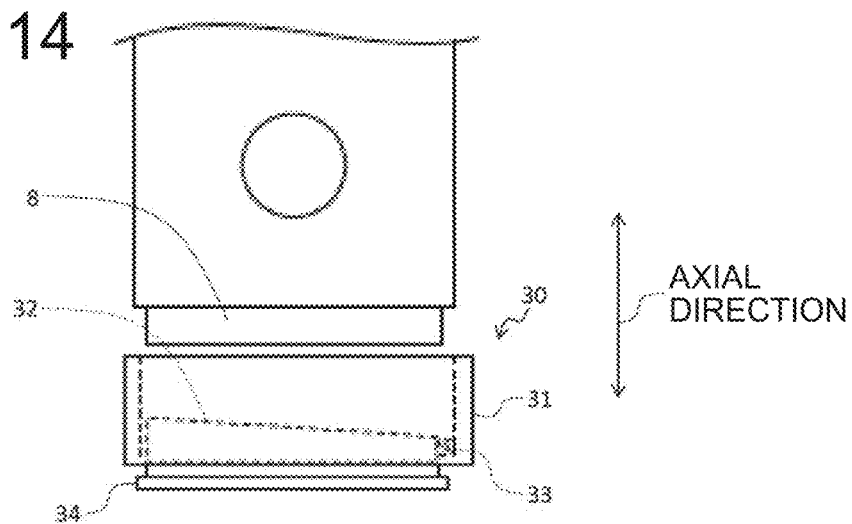
FIG. 14 illustrates a lens cap unit immediately before being attached to a housing.
Figure 15:
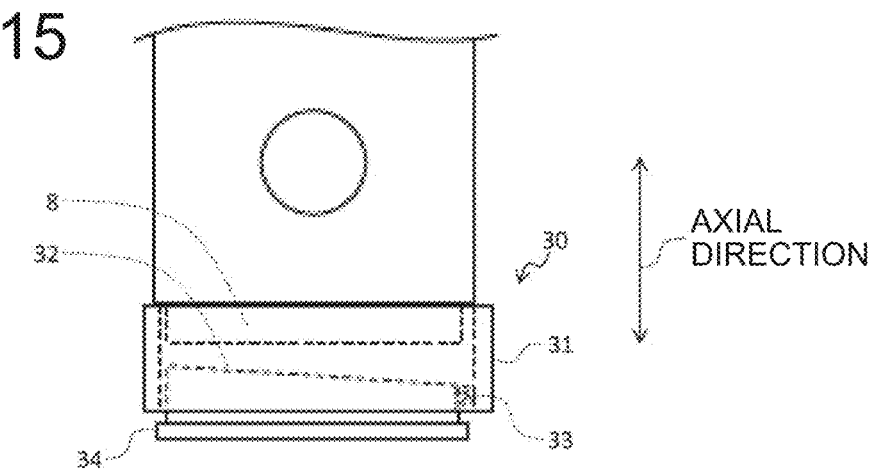
FIG. 15 illustrates a lens cap inserted over a housing.
Figure 16:
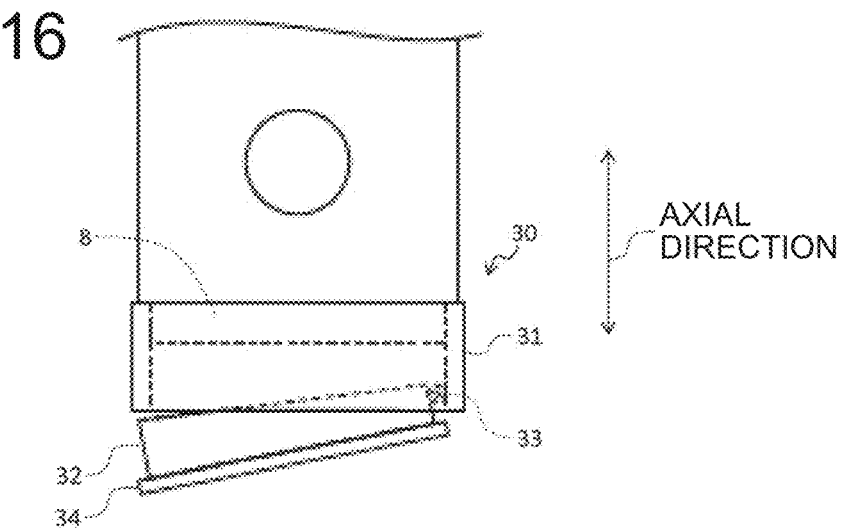
FIG. 16 illustrates a lens cap fixed to a housing.

In the following, a method of attaching the lens cap unit 30 to the housing 8 of the surgical microscope 1 (that is, step S21 to step S22 of FIG. 9) will be described with reference to FIG. 14 to FIG. 17. FIG. 14 illustrates the lens cap unit 30 immediately before being attached to the housing 8. FIG. 15 illustrates the lens cap 31 inserted over the housing 8. FIG. 16 illustrates the lens cap 31 fixed to the housing 8.

Firstly, as illustrated in FIG. 14, the operator sets the lens cap 31 made exposed from the inner side of the bag-shaped portion 21 (not illustrated in FIG. 14) below the housing 8.

The protective lens holder 32 in this state is at the attachment/detachment position. This causes the size of the inside diameter of the lens cap 31 which has been elastically expanded to be more than the size of the outside diameter of the housing 8.

Next, as illustrated in FIG. 15, the operator inserts the lens cap 31 over the housing 8 from the axial direction with the protective lens holder 32 being at the attachment/detachment position (S21). In this state, since the lens cap 31 has not been fixed to the housing 8 yet, the operator has to keep the position of the lens cap 31.

Next, as illustrated in FIG. 16, the operator pivots the protective lens holder 32 from the attachment/detachment position to the use position (S22). This reduces the diameter of the lens cap 31, and thus the lens cap 31 is fixed to the housing 8. Furthermore, the protective lens 34 is held with being tilted with respect to the optical axis L0 of the objective lens 6.

According to the embodiment described above, for example, the advantageous operations and effects can be obtained as follows.

According to the embodiment described above, the drape main body 20 is formed with the bag-shaped portion 21 and the band-shaped portion 22 so that the drape main body 20 can be prevented from hanging down and touching the floor, for example, during the process of attaching the microscope drape 10 to the surgical microscope 1 as illustrated in FIG. 7 and FIG. 8. This enables easy attachment of the microscope drape 10 to the surgical microscope 1 while keeping it clean.

Furthermore, according to the embodiment described above, the mark 26 is added to the outer edge of the opening 25 so that an operation of unwinding the drape main body 20 from the winding member 40 to the position of the opening 25 (step S1 in FIG. 9) is facilitated. This allows the operator to merely unwind the drape main body 20 until the mark 26 is exposed in step S1 of FIG. 9, for example, as illustrated in FIG. 6.

Still further, according to the embodiment described above, in the band-shaped portion 22, the coupling members 28a to 28c and 29a to 29c are provided on both sides in the width direction thereof so that the band-shaped portion 22 disposed along the upper surface of the surgical microscope 1 drapes the arms 2 to 5 and the like and is easily fixed to the surgical microscope 1. Still further, providing the coupling member 28a to 28c and 29a to 29c at a plurality of positions in the extension direction of the band-shaped portion 22, respectively, can reduce gaps in the band-shaped portion 22 covering the surgical microscope 1.

Still further, according to the embodiment described above, the microscope drape 10 (drape main body 20) wound around the winding member 40 is unwound along the upper surface of the surgical microscope 1, whereby an operation of covering the surgical microscope 1 with the drape main body 20 while keeping a clean condition can be made easy.

Furthermore, according to the embodiment described above, winding the microscope drape 10 (drape main body 20) around the winding member 40 in a state of being folded in three enables reduction in the size of the microscope drape 10 before use. This facilitates transportation and storage of the microscope drape 10.

Figure 17:
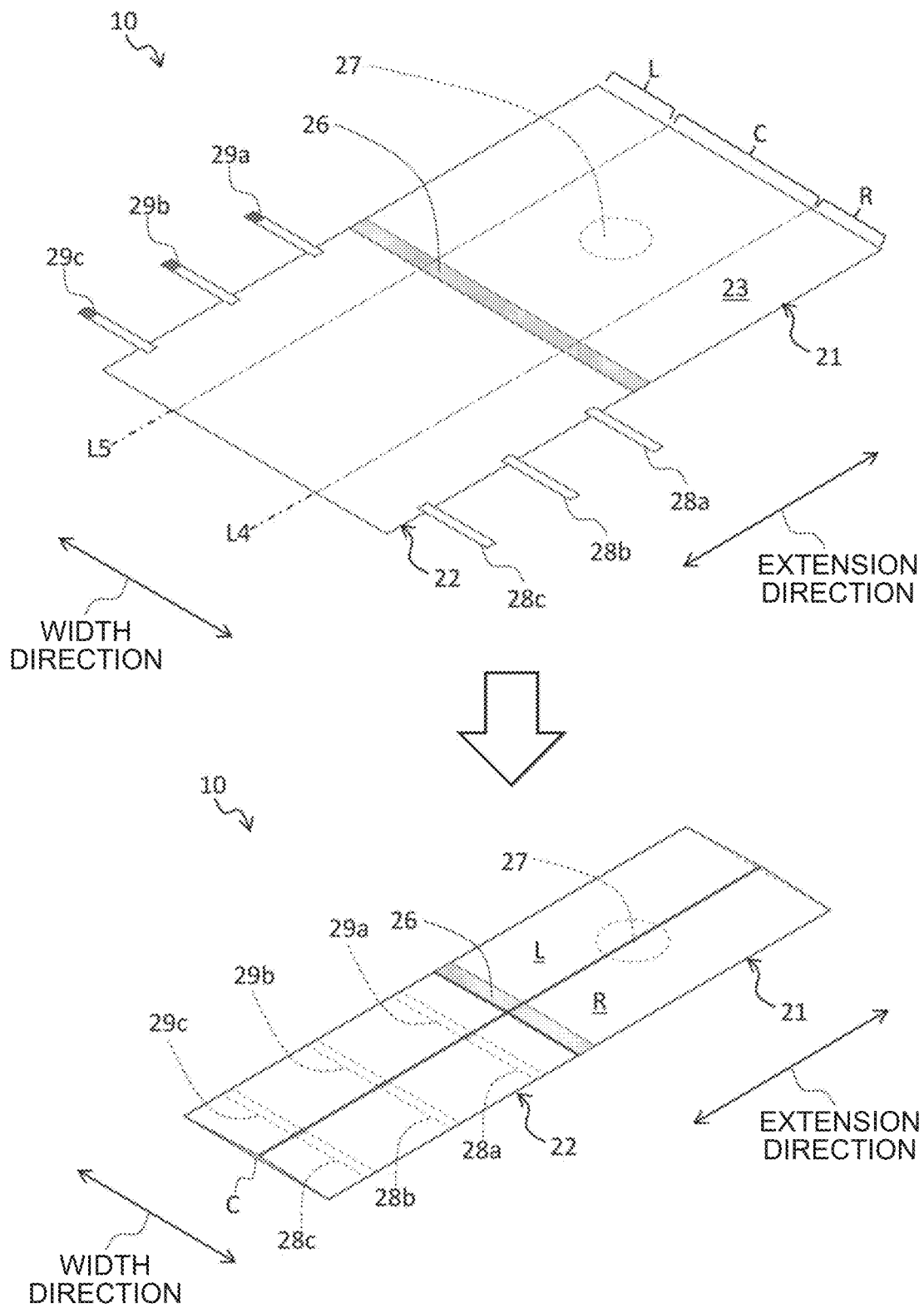
FIG. 17 illustrates a microscope drape folded in three without making end areas overlap to each other.
Figure 18:
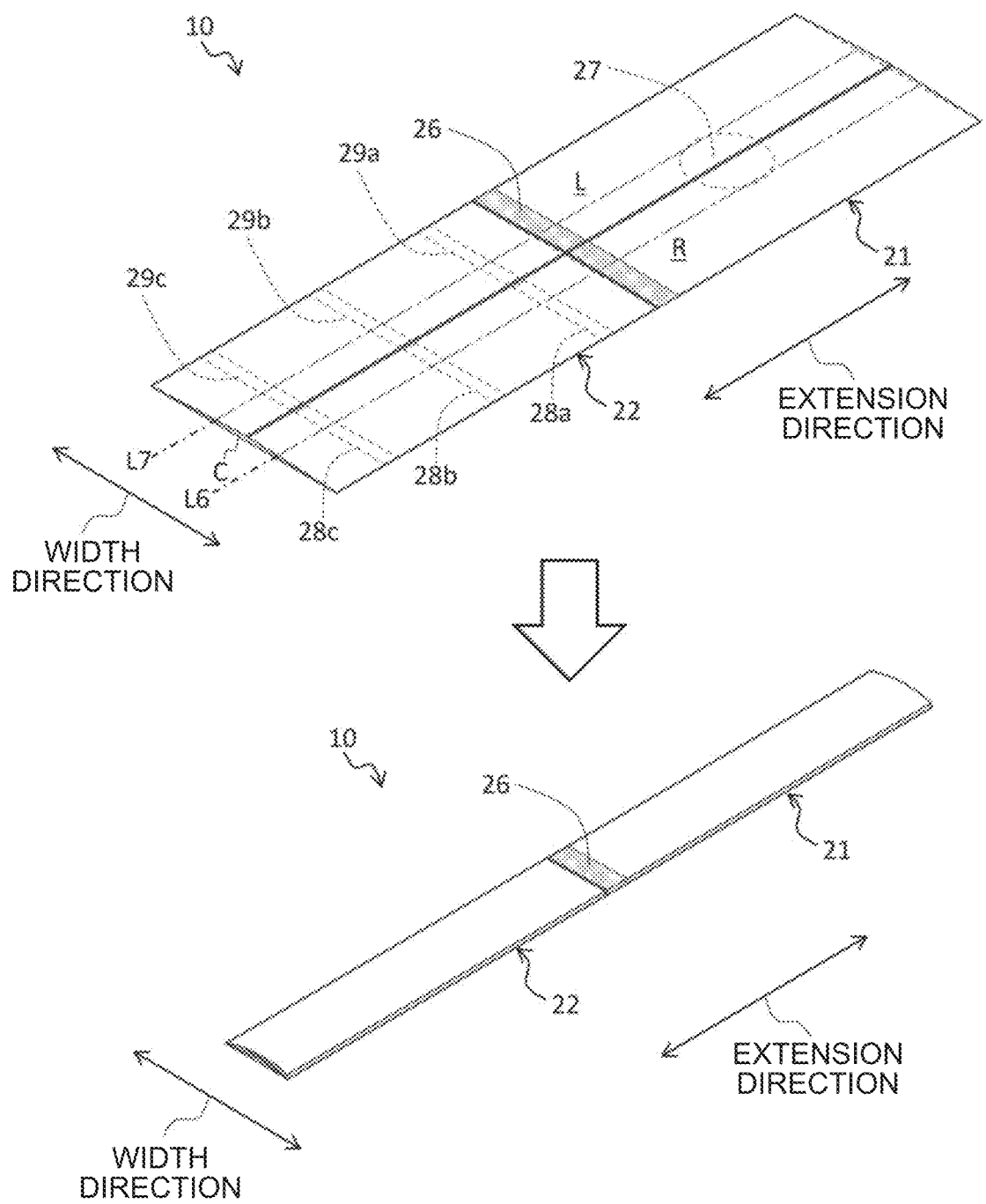
FIG. 18 illustrates a microscope drape of FIG. 17 folded further.

It should be noted that a specific method of folding back the microscope drape 10 (drape main body 20) is not limited to the example illustrated in FIG. 3 and FIG. 4. FIG. 17 illustrates the microscope drape 10 folded in three without making the areas R, L overlap to each other. FIG. 18 illustrates the microscope drape 10 of FIG. 17 folded further. In the following, the features common to those in the embodiment described above will not be repetitively explained in detail, but the differences will be mainly explained.

As illustrated in FIG. 17, the microscope drape 10 may be folded back toward the upper sheet 23 along imaginary lines L4, L5 extending in the extension direction from positions spaced apart to each other in the widthwise direction, respectively. The imaginary lines L4, L5 are further spaced apart in the widthwise direction as compared with the imaginary lines L1, L2 illustrated in FIG. 3. That is, in the area C, the size in the width direction is more than (as twice as) that in each of the areas R, L. As a result, as illustrated in the lower section of FIG. 17, the microscope drape 10 is folded in three such that the ends in the width direction of the areas R, L are in contact with each other at the center of the drape main body 20.

Furthermore, as illustrated in FIG. 18, the microscope drape 10 folded in three as illustrated in the lower section of FIG. 17 may be further folded back toward the upper sheet 23 along imaginary line L6, L7 extending in the extension direction from positions spaced apart to each other in the widthwise direction, respectively. This makes it possible to further reduce the size of the microscope drape 10 in the width direction.

Still further, according to the embodiment described above, a simple operation of pivoting the protective lens holder 32 from the attachment/detachment position to the use position causes the lens cap 31 to be fixed to the housing 8, and also the protective lens 34 to be tilted with respect to the optical axis L0 of the objective lens 6. Still further, the lens cap 31 can be inserted over the housing 8 from the axial direction with its diameter being elastically expanded so that it can be attached to the housing 8 without resistance. This can facilitate the operation of attaching the lens cap unit 30 to the surgical microscope 1.

Still further, according to the embodiment described above, the joint 33 is provided at a position of the protective lens holder 32 which has the shortest length in the axial direction so that the angle until the protective lens holder 32 is pulled out from the lens cap 31 (that is, angle difference between the attachment/detachment position and the use position) is reduced. This enables the user to freely select a tilt angle of the protective lens 34 at the use position.

Note that the use position of the protective lens holder 32 may not be set to one position. In other words, a tilt angle of the protective lens 34 which can be selected by the user is not limited to one angle. For example, the protective lens holder 32 may be pivoted with respect to the lens cap 31 to a first use position for causing the protective lens 34 to be tilted at a first angle (for example, 60°) with respect to the optical axis L0 and a second use position for causing the protective lens 34 to be tilted at a second angle (for example, 45°) with respect to the optical axis L0. Note that the first angle and the second angle are not limited to the examples described above as long as they are different angles from each other.

In the embodiment described above, the example in which the protective lens 34 is attached to the distal end in the axial direction of the protective lens holder 32 has been described. However, a specific method of making the protective lens holder 32 hold the protective lens 34 is not limited to the example described above. For example, the protective lens holder 32 may be provided with a slit that passes through the cylinder in the thickness direction so that the protective lens 34 can be inserted into and extracted from the slit. That is, the protective lens holder 32 may hold the protective lens 34 inserted into the slit. This allows the user to easily replace the protective lens 34 in accordance with the purpose of use.

Furthermore, the microscope drape 10 according to the present invention is not limited to the combination of the drape main body 20 illustrated in FIG. 2 to FIG. 5 and the lens cap unit 30 illustrated in FIG. 10 to FIG. 16. For example, the microscope drape 10 may include the drape main body 20 illustrated in FIG. 2 to FIG. 5 and a lens cap having a traditional cylindrical shape. Furthermore, for example, the microscope drape may include a drape main body having a traditional bag shape (cylindrical shape) and the lens cap unit 30 illustrated in FIG. 10 to FIG. 16.

REFERENCE SIGNS LIST

1 . . . surgical microscope, 2 to 5 . . . arm, 6 . . . objective lens, 7 . . . eyepiece lens, 8 . . . housing, 10 . . . microscope drape, 20 . . . drape main body, 21 . . . bag-shaped portion, 22 . . . band-shaped portion, 23 . . . upper sheet, 24 . . . lower sheet, 25 . . . opening, 26 . . . mark, 27 . . . through hole, 28a to 28c and 29a to 29c . . . coupling member, 30 . . . lens cap unit, 31 . . . lens cap, 32 . . . protective lens holder, 33 . . . joint, 34 . . . protective lens, 40 . . . winding member

The invention claimed is:

1. A microscope drape, comprising:
a detachable lens cap that is configured to be attached to a housing of an objective lens of a surgical microscope;
a protective lens that is attached to the lens cap so as to be arranged in a tilted state with respect to an optical axis of the objective lens, and configured to protect the objective lens; and
a drape main body that is configured to cover the surgical microscope, wherein
the drape main body includes:
a bag-shaped portion having a bag shape with one end is-formed to be an opening, to which the lens cap is attached; and
a band-shaped portion that extends to form a band shape from a portion in a circumferential direction of the opening of the bag-shaped portion,
in the bag-shaped portion, three sides of overlapping rectangular upper sheet and lower sheet are joined with each other, and another side defines the opening,
the band-shaped portion extends from the side of the upper sheet which defines the opening,
the lens cap is attached to a through hole that passes through a central portion of the lower sheet in a thickness direction,
a winding member around which the drape main body is wound, and
the drape main body has both ends in a width direction perpendicular to an extension direction of the band-shaped portion folded back toward a central portion of the upper sheet, and is wound around the winding member from a distal end of the band-shaped portion toward the bag-shaped portion.

2. The microscope drape according to claim 1, wherein a mark indicating an outer edge of the opening is disposed on the bag-shaped portion.

3. The microscope drape according to claim 1, wherein the drape main body includes a coupling member that couples both sides in the width direction of the band-shaped portion to each other.

* * * * *